(12) United States Patent
Nelson et al.

(10) Patent No.: US 8,449,548 B2
(45) Date of Patent: May 28, 2013

(54) BROACH HANDLE WITH FLEXURE SPRING

(75) Inventors: Andrew Nelson, Upper Saddle River, NJ (US); Michael A. McGovern, Wyckoff, NJ (US); Roy Splieth, Central Valley, NY (US); Gennaro A. Barile, Secaucus, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 577 days.

(21) Appl. No.: 12/644,132

(22) Filed: Dec. 22, 2009

(65) Prior Publication Data

US 2011/0152954 A1 Jun. 23, 2011

(51) Int. Cl.
*A61F 2/46* (2006.01)

(52) U.S. Cl.
USPC ....................................................... 606/86 R

(58) Field of Classification Search
USPC ............... 606/79–85, 280–299, 86 A, 86 B, 606/99; 294/104
See application file for complete search history.

(56) References Cited

U.S. PATENT DOCUMENTS

| | | | |
|---|---|---|---|
| 4,583,270 A | 4/1986 | Kenna | |
| 4,765,328 A | 8/1988 | Keller et al. | |
| 4,990,149 A | 2/1991 | Fallin | |
| 5,089,003 A | 2/1992 | Fallin et al. | |
| 5,147,408 A | 9/1992 | Noble et al. | |
| 5,190,550 A | 3/1993 | Miller et al. | |
| 5,324,293 A * | 6/1994 | Rehmann | 606/85 |
| 5,443,471 A | 8/1995 | Swajger | |
| 6,113,605 A | 9/2000 | Storer | |
| 6,205,884 B1 * | 3/2001 | Foley et al. | 74/544 |
| 6,206,882 B1 * | 3/2001 | Cohen | 606/283 |
| 6,337,142 B2 | 1/2002 | Harder et al. | |
| 6,626,913 B1 | 9/2003 | McKinnon et al. | |
| 7,569,055 B2 | 8/2009 | Zander et al. | |

* cited by examiner

*Primary Examiner* — Andrew Yang
*Assistant Examiner* — Diana S Jones
(74) *Attorney, Agent, or Firm* — Lerner, David, Littenberg, Krumholz & Mentlik, LLP

(57) ABSTRACT

An instrument for holding a surgical tool or bone implant includes a handle with a bearing surface formed in one end for engaging the surgical tool. An elastically deformable plate is mounted on the handle body the plate having a catch element formed on a leading end thereof adapted to engage a coupling element formed on the surgical tool. The elastically deformable plate includes a cam follower formed in a recess thereon and includes a deformable spring section intermediate the can elements and the plate end with the catch element. An elongated pivotable loading member is rotatably mounted on the handle body. The loading member includes a cam surface for engaging the cam follower surface on the deformable plate. The cam surface on the loading member is shaped to elastically deform the elastically deformable plate section in a direction away from the plate catch element to thereby load and maintain a connecting force between the plate and the surgical tool or bone implant.

19 Claims, 9 Drawing Sheets

BROACH HANDLE WITH FLEXURE SPRING

BACKGROUND OF THE INVENTION

This invention relates to a surgical tool for engaging a rasp or broach during a surgical procedure. More particularly, the invention relates to a handle that can selectively releasably hold a surgical instrument such as a broach or rasp during the preparation of a bone canal.

Implantations of prosthetic implants such as femoral components or humeral components require forming a shaped cavity in the proximal femur or humerus. Often as part of this procedure a broaching or rasping operation is performed utilizing a broach or rasp having the shape of the femoral prosthetic component or humeral prosthetic component to produce a matching cavity or a cavity slightly larger when using bone cement. Broach holding tools or instruments have been provided to releasably engage multiple different size broaches or rasps. These holding instruments have various methods of locking the broach or rasp to the handle.

Typical broach handles are shown, for example, in U.S. Pat. Nos. 5,089,003; 5,190,550; 5,324,293; and 5,443,471. All of these systems include structure for selectively releasing the broach from the handle after being used with the broach locked to the handle. However, none of the prior art discloses a simple design which allows for the handle to be preloaded to the broach with a handle having a minimal number of parts and which handle allows for the simple and reliable cleaning thereof after use.

BRIEF SUMMARY OF THE INVENTION

It is one aspect of the invention to provide an apparatus for holding a surgical broach during a broaching procedure. The apparatus may have a handle body having a handle bearing surface formed on one end of the body for acting on a complimentary bearing surface on the broach. An elastically deformable plate is mounted on the handle body in a manner which allows the plate to slide with respect to the body. The body may have a u-shape with an open side capable of receiving the plate. A plate is elastically deformable and has a catch element formed at a leading first end thereof adapted to engage a latch element formed on the broach. The elastically deformable plate has a spring section that may elongate elastically when applying a force between the broach and the handle body. An elongated loading member is pivotally rotatably connected to the handle body. The loading member has a cammed surface for engaging a cam follower surface on the elastically deformable plate and rotation of the cam moves a second end of the plate opposite the end with the catch element away from the broach contacting surfaces. This results in the catch element on the plate pulling on the latch element on the broach and preloading the broach against the handle broach contacting surface. This preloaded force is maintained during the broaching operation and is sufficient to prevent any separation between the broach and the broach handle during use.

When the broach or other tool is attached the elongated loading member has a first rotational position spaced from the handle body where the elastically deformable plate is in a relaxed state and has a second position, where rotated adjacent the handle body, where the elastically deformable plate is in a tensioned state. The tensioned state results from the movement of the second end of the elastically deformable plate away from the first plate end adjacent the broach handle body interface about the spring section of the plate. The cam surface on the elongated loading member includes a detent position adjacent the area of the cam surface which contacts the cam follower on the elastically deformable plate when in the fully tensioned state. The detent, which may be in the form of a protrusion from the cam surface, prevents the unintentional rotation of the loading member away from the handle body during use. Thus, the tension between the broach and the handle body is maintained.

The elastically deformable plate has opposite first and second sides and includes a spring section having slots extending from the first side to a position beyond a central longitudinal axis of the elastically deformable plate and terminating at a predetermined distance from the second plate side. Likewise, the plate has slots which extend from the second side toward the first side passing beyond the central longitudinal axis and stopping at a predetermined distance from the first side. In another embodiment only one slot would extend beyond the central axis but still overlapping the shorter slots extending inwardly from the opposite side. The slots are spaced axially along the longitudinal axis a distance allowing the elastically deformable plate spring section to expand under the force developed by the cam surface of the loading member against the cam follower on the elastically deformable plate. In one embodiment, the slots are perpendicular to the longitudinal axis thus extending in parallel. In addition, it has been found that having at least two and preferably three slots extending inwardly from both the first and the second sides produces sufficient elasticity to provide the necessary loading force between the broach handle and the broach. To ensure proper guidance of the elastically deformable plate within the handle body, the handle body may be made hollow and act as a track for guiding the sliding of at least the second end of the elastically deformable body when the spring section is elongate. In addition, pins can be mounted in slots formed in the elastically deformable body which act as guides and as stop surfaces to limit the expansion, and therefore the force produced, by the elongation of the spring section of the elastically deformable plate member. To ensure movement of the elastically deformable plate member toward the contact surface, a spring may be mounted between the second end of the elastically deformable plate and the handle body to move the elastically deformable body toward the tool contact end of the handle including a recess to receive the pin extending from the handles.

In another aspect of the invention the handle could be used to hold an implant during insertion into, for example, a femoral canal. The femoral implant would have a proximal portion designed to mate with the handle

DETAILED DESCRIPTION

Figure 1:
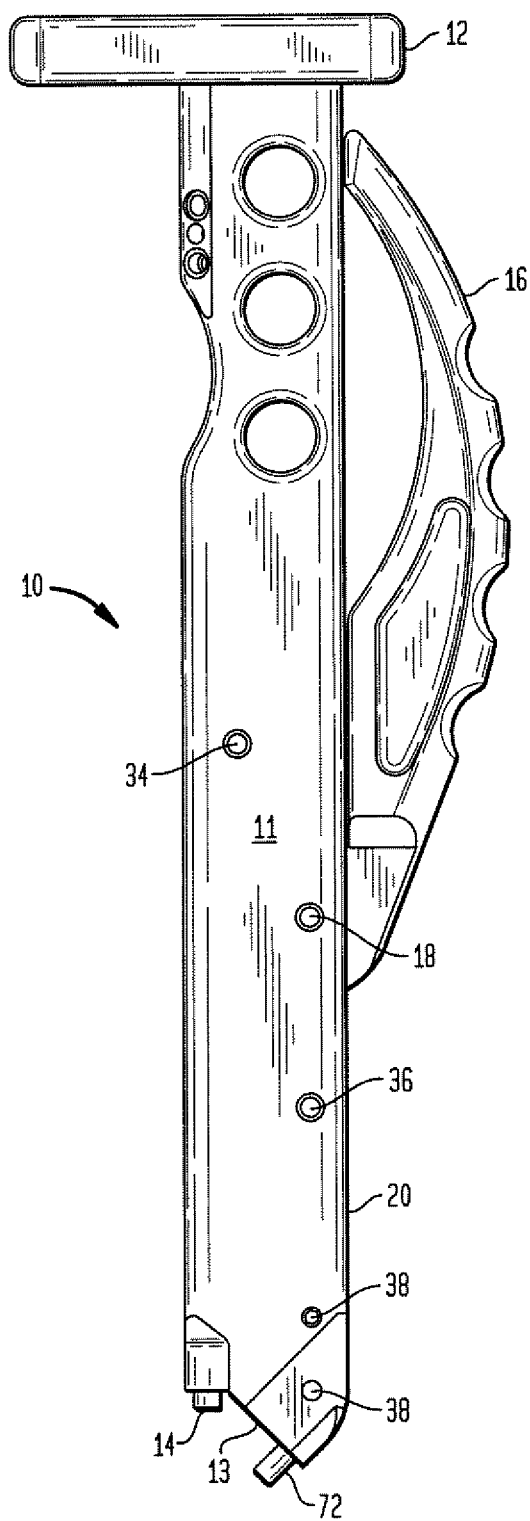
FIG. 1 is an elevation view of the apparatus for holding a bone cutting tool or bone implant of the present invention including a handle body, resilient plate and a loading member.
Figure 2:
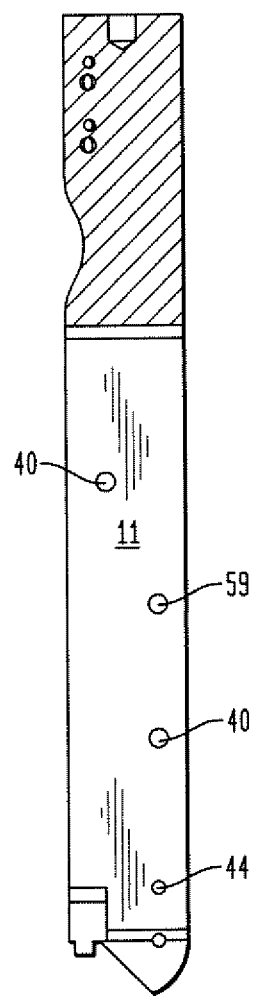
FIG. 2 is an elevation view of a handle body utilized in the assembly of FIG. 1.
Figure 3:
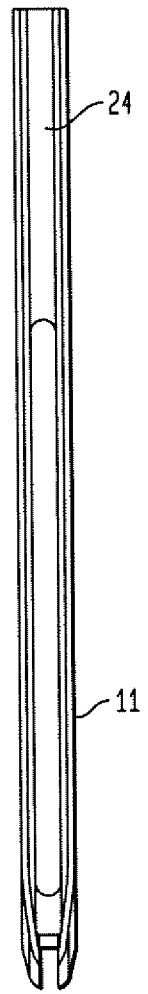
FIG. 3 is an end view of the handle body of FIG. 2 showing an open slot for receiving a deformable plate.

Referring to FIG. 1, there is shown a surgical tool generally denoted as 10 for engaging a surgical tool such as a rasp or broach. As indicated above, the handle could also engage a bone implant such as a humeral or femoral implant. Thus the following description applies equally to an implant or other device for insertion into an intramedullary canal. Surgical tool handle 10 has a handle body 11, including an impaction plate 12 at a second end thereof and a broach contact surface 13 at a leading first end and a broach contact extension element 14 extending from the first end thereof. Mounted within the hollow handle body 11 is a lever loading member 16 which is pivotally connected to body 11 by pivot pin 18. Loading member 16 is ergonomically designed to allow hand pivoting about pin 18 toward and away from a side 20 of the body. Referring to FIGS. 2 and 3, it can be seen that body 11 has a cavity 24 which forms a generally U-shaped tract for holding and guiding a deformable plate generally denoted as 26 and shown in FIG. 4A.

Figure 4A:
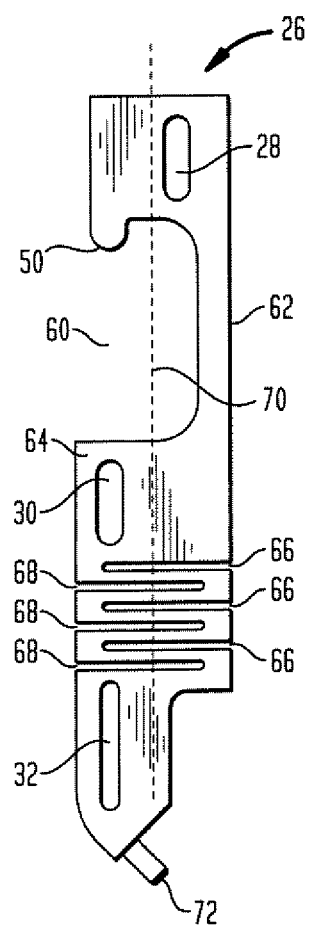
FIG. 4A is an elevation view of the elastically deformable plate received within the handle body.
Figure 4B:
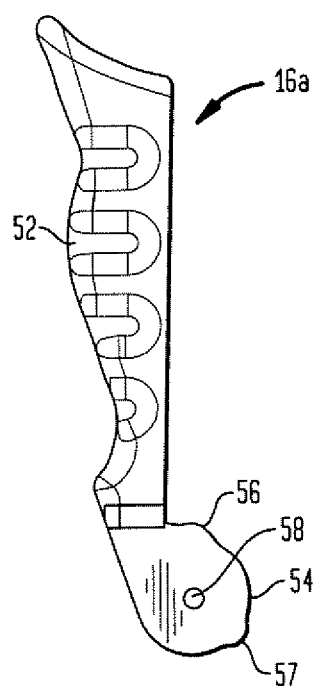
FIG. 4B is an elevation view of the loading member including cam of the apparatus of FIG. 1.

Referring to FIGS. 4A and 4B, plate 26 includes a plurality of longitudinally extending elongated bores 28, 30, and 32. These elongated bores engage pins 34, 36, and 38, respectively. Pins 34, 36, and 38 are press fit through openings 40, 42, and 44 of handle body 11 after plate 26 has been inserted into U-shaped cavity 24 during assembly. Deformable plate 26 includes a cut out portion 60 including cam element 50 which acts as a cam follower for the cam surface 54 shown in FIG. 4B. As will be discussed below rotation of the loading member 16 causes movement of the part of plate 26 with respect to handle body 11 by the engagement of the cam surface 54 with cam follower 50. Plate 26 includes side surfaces 62 and 64 which define a section having at least two overlapping transverse slots 66 extending inwardly past a centerline 67 towards side 64. Similarly, at least two slots extend inwardly from side 64 past centerline 67 towards side 62. Preferably there are three slots 66 and 68 although even more slots may be utilized. The plate 26 has a first end including a catch element 72 adapted to engage a latch element on a broach. When engaged on a broach the slots 68 can expand in width allowing the upper part of plate 26 to move toward the impaction end of the handle.

Figure 5:
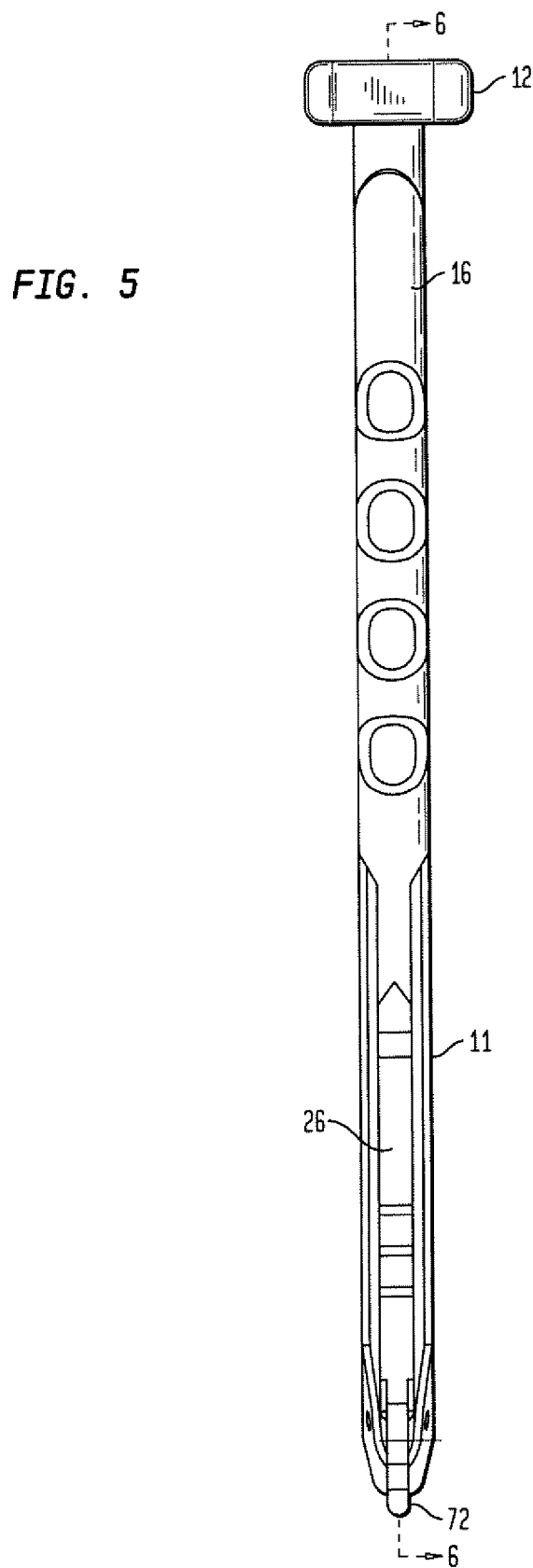
FIG. 5 is an end view showing the assembly of the handle body, loading member, and the elastically deformable plate member mounted within the handle body slot.

Referring to FIG. 4B there is shown an alternate loading member or lever generally denoted as 16a, which includes a gripping area 52 and a cam surface 54 at an end thereof. The only difference between loading member or lever 16 and 16a is the design of the gripping area 52. Cam surface is identical in each lever. Cam surface 54 includes a detent protrusion 56 and a stop 57. Cam surface 54 is rotatable about pivot point 58 which, when assembled to body 11 receives pivot pin 18. As can be seen in FIG. 2, handle body 11 includes a bore 59 in which pivot pin 18 is mounted after the loading member 16 is assembled within body 11. FIG. 5 is an end view of the fully assembled broach handle shown in FIG. 1.

Figure 6A:
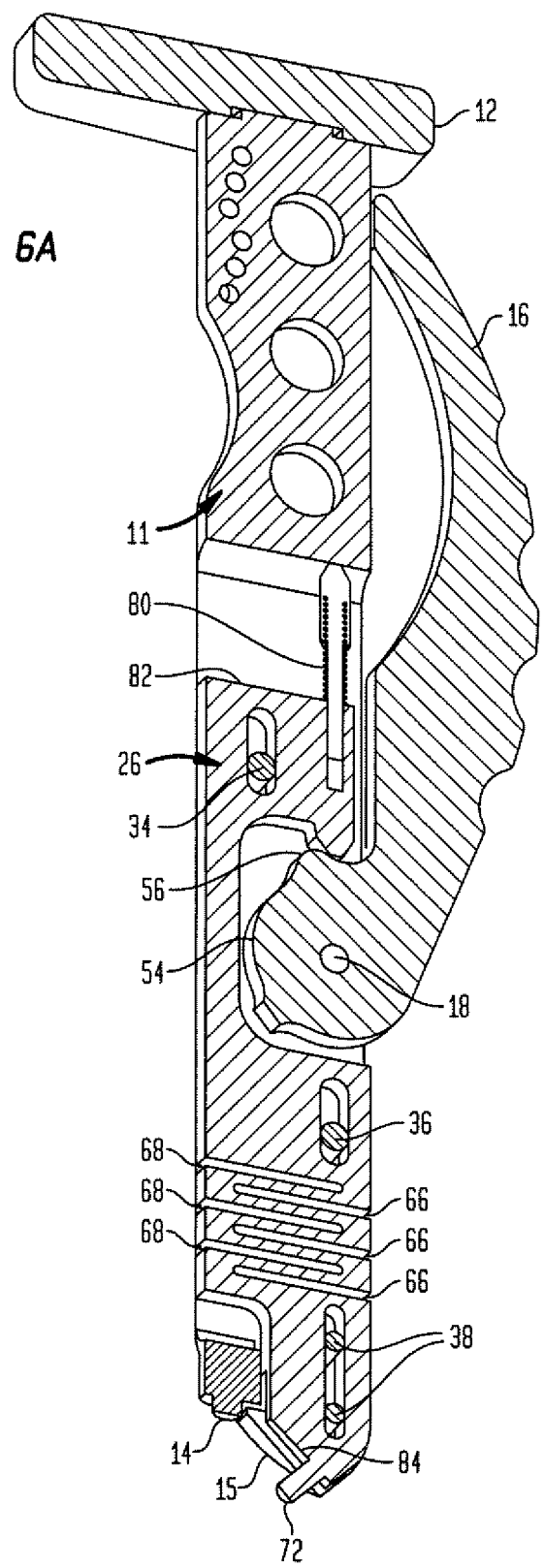
FIG. 6A is a cross-sectional view of the assembly of FIG. 5 along lines 6-6.

Referring to FIG. 6A, there is shown a partial cutaway view showing the assemblies of FIGS. 1 and 5. As discussed with reference to FIG. 4A, there is shown cam follower 50, which engages cam surface 54 on loading member 16. Cam follower 50 extends into a cavity 60, which receives the cam surface 54 of loading member 16 and allows sufficient space for loading member 16 to rotate with respect to handle body 11. When the loading member 16 is rotated clockwise in FIG. 6 a second end 69 of elastically deformable plate 26 moves away from the first end with catch 72 by expanding the series of slots 66 and 68, which extend inwardly from the first and second sides 62 and 64, respectively. It has been found that suitable slots 66 and 68 may extend within 0.22 inches of the opposite sides 62 or 64 and have central axes between slots spaced 0.144 inches with a slot width of 0.064 inches. Thus, it has been found that these dimensions on a plate having a width between sides 62 and 64 of approximately one inch and a plate thickness of 0.246 inches provides a plate with sufficient flexibility and force generation to be used in the handle broach assembly in a manner as will be discussed below. Other dimensions could be used that produce sufficient force on the handle broach joint on elongation of the spring section of plate 26.

Figure 6B:
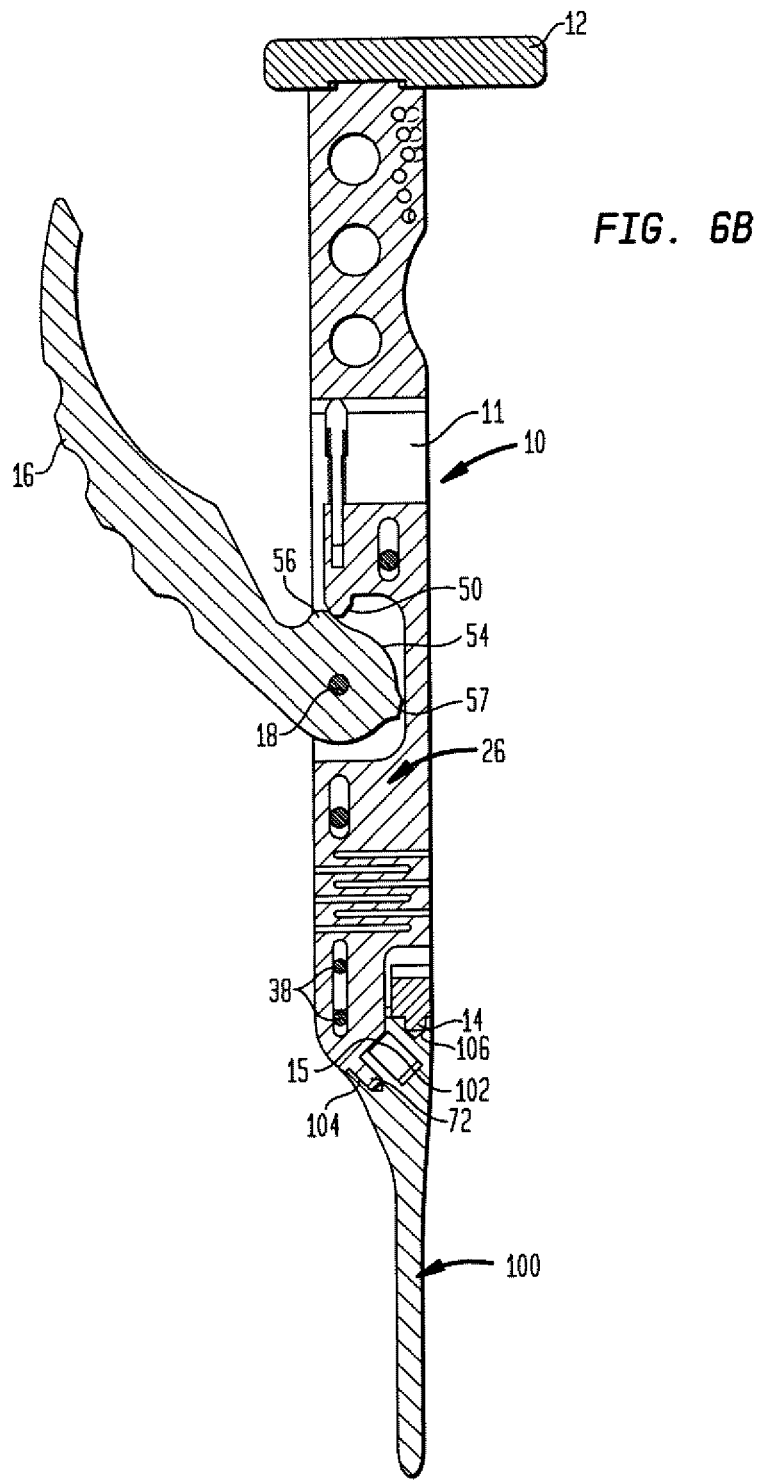
FIG. 6B is a cross-sectional view of the assembly of FIG. 5 connected to a broach.

Referring to FIG. 6B there is shown the surgical tool 10 connected to a broach 100. Broach 100 includes a surface 102 for engaging surface 15 of handle body 11. Broach 100 also includes a recess or bore 104 for receiving catch element 72 of deformable plate 26. Broach 100 also includes a recess 106 for receiving element 14 of handle body 11. Also shown in FIG. 6B is loading member or lever 16 immediately prior to detent cam surface 56 engaging cam follower 50. Recess or bore 104 acts as a latch element into which catch element 72 is inserted on assembly. Catch element 72 can be a pin having a diameter to mate with bore 104.

Again referring to FIG. 6A, handle body 11 is shown connected to an impact portion 12 at one end and including broach contact surface 14 and 15 at the opposite end. As can be seen, loading member or lever 16 is pivotally mounted to handle body 11 via pivot pin 18. Cam follower 50 is shown in a stable position beyond detent 56, which occurs when the elastic loading plate 26 is in a fully tensioned position. In this position, tool catch member 72 is fully engaged with the catch bore 104 of broach 100. When fully engaged, surface 15 of body 11 also engages complimentary surface 102 on broach 100. As can be seen, pins 34, 36, and 38 serve to guide the movement of plate 26 on body 11 as well as limit the elastic elongation of plate 26. When fully loaded as shown in FIG. 6A, slots 66 and 68 expand slightly in width with pin 36 limiting the expansion of the plate 26. In order to ensure that plate 26 unloads properly when the loading member 16 is in the open position, opposite that shown in FIG. 6A, a spring 80 is provided which acts between handle body 11 and surface 82 of plate 26. In order to ensure deformable plate 26 does not engage the contact surface on the broach, a surface 84 of plate 26 is spaced inwardly of surface 15 so that when fully tensioned the forces developed act between the handle body 11 surface 15 and surface 102 of the broach. This also ensures catch 72 can apply full force to latch bore 104.

Figure 7:
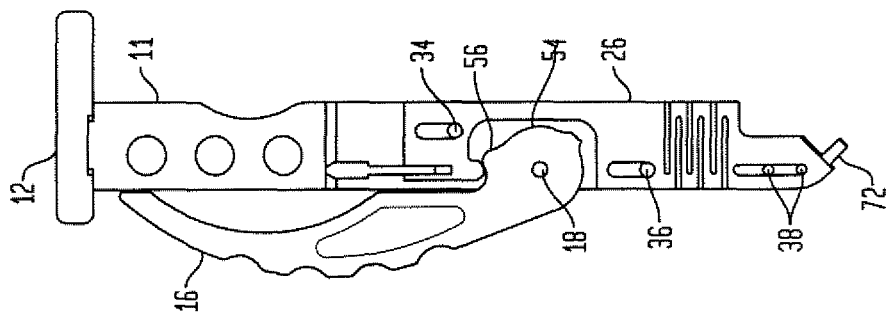
FIGS. 7 through 9 show the loading operation for applying a tensioning force to a surgical tool, such as a broach.
Figure 8:
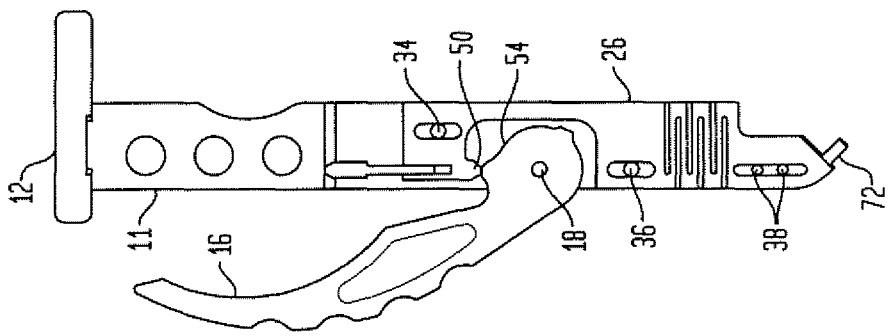
Figure 9:
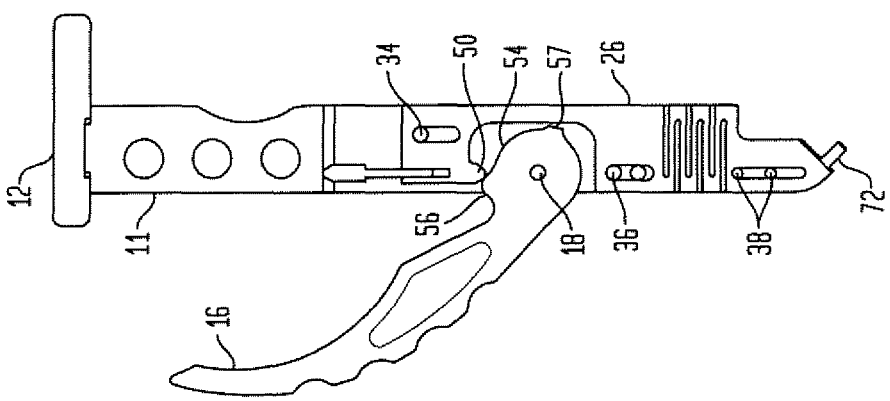

Referring to FIGS. 7 through 9, there is shown the operation of the broach handle 10 of the present invention. As shown in FIG. 7, the loading member or handle 16 is in the open position allowing the spring portion of the elastically deformable plate 26 to be in a relaxed condition. A stop 57 prevents the handle 10 from rotating fully downward to keep the handle in a position where it can easily be gripped. Loading member 16 is then rotated toward handle body 12 with the cam surface 54 shaped to engage cam follower 50 and deform slots 66, 68 which allows second end 82 of plate 26 to move longitudinally along the handle body 11 toward impaction head 12 thereof. When catch 72 engages the corresponding latch bore 104 on the broach, the broach is moved by rotation of loading member 16 against surfaces 14 and 15 of handle body 11 and slots 68 and 66 widen producing a force between the handle body 11 and the broach. As shown in FIG. 9, further rotation of loading member 16 toward body 11 causes the maximum movement of the expansion of the spring section of plate 26 about slots 66 and 68 thereby producing a maximum force on surfaces 14, 15, and the corresponding broach surface 102. At this point detent 56 passes beyond cam follower 50 to hold the loading member 16 in position. The maximum force is produced by the slotted spring just prior to the loading member 16 to the fully closed position as shown in FIG. 9. The loading member 16 "snaps" closed (FIG. 9) providing a tactile feedback to the user and insuring that the lever 16 does not inadvertently open during use. The "snap" is not covered as much by the detent 56 as by a decrease in height of the cam lobe. Note that no spring force will be produced by clockwise rotation of the lever 16 unless a broach or implant is attached to the handle. In this position, the broach handle and broach assembly may be used in the standard manner in preparing a femoral canal or humeral canal to receive an implant. When the loading member 16 is released by rotating counter clockwise, spring 80 ensures that the deformable plate 26 returns to its relaxed position. Spring 80 may be a coil or leaf spring or even an integrated flexure spring.

Figure 10:
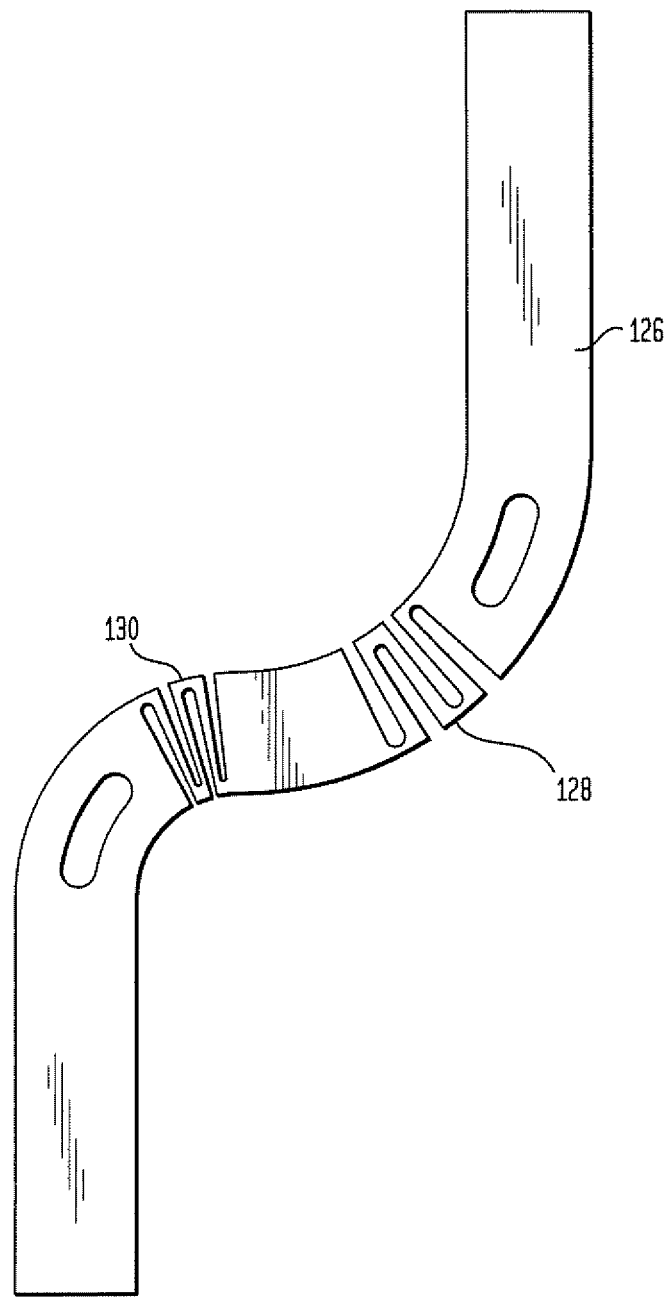
FIG. 10 is a view of an alternate deformable plate design for use with a curved handle.

Referring to FIG. 10 there is schematically shown a curved plate 126 which can be used with a handle (not shown) having a curve or bend. Such a curved or bent handle may be useful in avoiding anatomic structure during broaching. As seen in FIG. 10 two sets of slots 128 and 130 are provided which are loaded in a manner similar to the slots of plate 26. Various other features of plate 26 may be included in page 126.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for holding a surgical broach or implant during a surgical broaching procedure, the apparatus comprising:
   (a) a handle body;
   (b) a handle bearing surface formed on a broach or implant holding end of the handle body, the handle bearing surface being adapted to mate with a corresponding bearing surface formed on a surgical broach or implant when the broach or implant is in an insertion position with respect to the handle body;
   (c) an elastically deformable plate slidably mounted on the handle body, cooperating guide elements on the handle and plate permitting movement therebetween with respect to a longitudinal axis, the plate having a catch element formed thereon and adapted to catch on a latch element formed on the broach or implant, the plate member for catching on the latch element of the broach or implant for connecting the broach or implant bearing surface to the handle body bearing surface when the broach or implant is in the insertion position, and the plate capable of elongating elastically with respect to the longitudinal axis; and
   (d) a loading member rotatably connected to the handle body, the loading member having a surface thereon for engaging a surface on the elastically deformable plate and increasing the length of the plate by moving a first end of the plate along the longitudinal axis away from the handle body bearing surface for applying and maintaining a force so that the plate catch element connects the broach or implant in the insertion position with respect to the handle body wherein the elastically deformable plate has opposite first and second sides and includes a section having slots extending from the first and second plate sides to a position beyond the longitudinal axis of the elastically deformable plate and terminating at a distance from the opposite plate side.

2. The apparatus as set forth in claim 1 wherein the slots are perpendicular to the central longitudinal axis.

3. The apparatus as set forth in claim 1 wherein at least two slots extend from the first side towards the second side and at least two slots extend from the second side towards the first side.

4. The apparatus as set forth in claim 3 wherein the slots are parallel.

5. The apparatus as set forth in claim 4 wherein the slots are perpendicular to the central longitudinal axis.

6. The apparatus as set forth in claim 1 wherein the elastically deformable plate is slidably mounted within a track in the handle body.

7. The apparatus as set forth in claim 6 further comprising a spring mounted between the handle body and the elastically deformable plate for biasing the elastically deformable plate towards the bearing surface of the handle.

8. The apparatus as set for in claim 1 wherein the elongated loading member has a first rotational position wherein the elastically deformable plate is in a relaxed state and in a second position adjacent the handle body when the elastically deformable plate is in a tensional state.

9. The apparatus as set forth in claim 1 wherein the surface on the elongated loading member includes a detent portion adjacent an area of the surface contacting the deformable plate surface when in the second position.

10. An apparatus for holding a device for insertion in an intramedullary canal comprising:
    a handle having a gripping portion and a surface for contacting the device for insertion into the canal;
    a plate mounted on the handle for movement with respect to a longitudinal axis of the handle, the handle and plate having cooperating guide elements for permitting relative movement only with respect to the longitudinal axis, the plate having a catch element at a first end adjacent the handle device contacting surface and an elastically deformable spaced from the first plate end in a direction toward the handle gripping portion;
    the device for insertion into an intramedullary canal having a surface for engaging the handle device contacting surface and having a latch element adapted to engage the catch element on the plate first end; and
    a loading member pivotally connected to the handle, the loading member having a surface thereon engaging a surface of the elastically deformable plate and expanding the elastically deformable section thereby increasing the length of the plate along the longitudinal axis of the handle upon rotation of the loading member to connect the handle and the device to be inserted into the canal, wherein the elastically deformable section of the plate has opposite first and second sides and includes a section having slots extending from the first and second plate sides to a position beyond a central longitudinal axis of the plate and terminating at a distance from the opposite plate side.

11. The apparatus as set forth in claim 10 wherein the slots are perpendicular to the central longitudinal axis.

12. The apparatus as set forth in claim 10 wherein at least two slots extend from the first side towards the second side and at least two slots extend from the second side towards the first side.

13. The apparatus as set forth in claim 12 wherein the slots are parallel.

14. The apparatus as set forth in claim 13 wherein the slots are perpendicular to the central longitudinal axis.

15. The apparatus as set forth in claim 10 wherein the plate is slidably mounted within a track in the handle body.

16. The apparatus as set forth in claim 15 further comprising a spring mounted between the handle body and the plate for biasing the plate towards the total contacting surface of the handle.

17. The apparatus as set forth in claim 10 wherein the elongated loading member has a first rotational position wherein the plate elastically deformable section is in a relaxed state and in a second position adjacent the handle body when the elastically deformable section is deformed into a tensional state.

18. The apparatus as set forth in claim 10 wherein the surface on the elongated loading member includes a detent portion adjacent an area of the surface contacting the plate surface when in the second position.

19. An apparatus for holding a surgical broach or implant during a surgical broaching procedure, the apparatus comprising:
   (a) a handle body;
   (b) a handle bearing surface formed on a broach or implant holding end of the handle body, the handle bearing surface being adapted to mate with a corresponding bearing surface formed on a surgical broach or implant when the broach or implant is in an insertion position with respect to the handle body;
   (c) an elastically deformable plate slidably mounted on the handle body, cooperating guide elements on the handle and plate permitting movement therebetween with respect to a longitudinal axis, the plate having a catch element formed thereon and adapted to catch on a latch element formed on the broach or implant, the plate member catch element catching on the latch element of the broach or implant for connecting the broach or implant bearing surfaces to the handle body bearing surface when the broach or implant is in the insertion position, and the plate capable of elongating elastically with respect to the longitudinal axis; and
   (d) a loading member rotatably connected to the handle body, the loading member having a surface thereon for engaging a surface on the elastically deformable plate and increasing the length of the plate by moving a first end of the plate with respect to the longitudinal axis away from the handle body bearing surface for applying and maintaining a force so that the plate catch element connects the broach or implant in the insertion position with respect to the handle body wherein the elastically deformable plate is slidably mounted within a track in the handle body and further comprising a spring mounted between the handle body and the elastically deformable plate for biasing the elastically deformable plate towards the bearing surface of the handle, wherein the elastically deformable section of the plate has opposite first and second sides and includes a section having slots extending from the first and second plate sides to a position beyond a central longitudinal axis of the plate and terminating at a distance from the opposite plate side.

\* \* \* \* \*

UNITED STATES PATENT AND TRADEMARK OFFICE
CERTIFICATE OF CORRECTION

PATENT NO.           : 8,449,548 B2  
APPLICATION NO.      : 12/644132  
DATED                : May 28, 2013  
INVENTOR(S)          : Andrew Nelson et al.

Page 1 of 1

It is certified that error appears in the above-identified patent and that said Letters Patent is hereby corrected as shown below:

In the Claims

Column 5, line 55 "for" should read --catch element--.
Column 5, line 57 "surface" should read --surfaces--.
Column 6, line 25 "for" should read --forth--.
Column 6, line 36 "having a gripping" should read --having a body with a gripping--.
Column 6, line 44 "deformable spaced" should read --deformable section--.
Column 6, line 44 "first plate end" should read --plate--.

Signed and Sealed this
Eighth Day of September, 2015

Michelle K. Lee
*Director of the United States Patent and Trademark Office*